(12) United States Patent
Freue et al.

(10) Patent No.: US 9,125,957 B2
(45) Date of Patent: Sep. 8, 2015

(54) APPLIANCE FOR DISINFECTING HAND-HELD DEVICES

(71) Applicant: Angelini Pharma, Inc., Gaithersburg, MD (US)

(72) Inventors: Guillermo J. Cohen Freue, Louisville, KY (US); Gary Joel Mishkin, Gaithersburg, MD (US); William Warren Lynn, Hilton Head Island, SC (US)

(73) Assignee: ANGELINI PHARMA, INC., Gaithersburg, MD (US)

( * ) Notice: Subject to any disclaimer, the term of this patent is extended or adjusted under 35 U.S.C. 154(b) by 0 days.

(21) Appl. No.: 14/401,586

(22) PCT Filed: May 17, 2013

(86) PCT No.: PCT/US2013/041568
§ 371 (c)(1),
(2) Date: Nov. 17, 2014

(87) PCT Pub. No.: WO2013/173703
PCT Pub. Date: Nov. 21, 2013

(65) Prior Publication Data
US 2015/0115172 A1    Apr. 30, 2015

Related U.S. Application Data

(60) Provisional application No. 61/789,704, filed on Mar. 15, 2013, provisional application No. 61/648,759, filed on May 18, 2012.

(51) Int. Cl.
*A61L 2/00* (2006.01)
*A61L 2/10* (2006.01)
*G01J 3/10* (2006.01)
*C09D 5/14* (2006.01)

(52) U.S. Cl.
CPC .... *A61L 2/10* (2013.01); *C09D 5/14* (2013.01)

(58) Field of Classification Search
CPC ............. A23L 3/28; A23L 3/26; B65B 55/02; B65B 55/16; A61L 12/06; A61L 12/063; A61L 12/086; A61L 2/08; B01D 2259/804
USPC ............... 422/24, 186.3; 250/453.11, 454.11, 250/455.11, 504 R, 492.1
See application file for complete search history.

(56) References Cited

U.S. PATENT DOCUMENTS

| | | | | |
|---|---|---|---|---|
| 4,877,964 A * | 10/1989 | Tanaka et al. | ............ | 250/455.11 |
| 5,958,336 A * | 9/1999 | Duarte | ............................. | 422/24 |
| 6,132,784 A * | 10/2000 | Brandt et al. | .................. | 426/248 |
| 2003/0170357 A1* | 9/2003 | Garwood | ....................... | 426/392 |
| 2009/0130169 A1 | 5/2009 | Bernstein | | |

FOREIGN PATENT DOCUMENTS

WO    03092886 A1    11/2003
WO    2010044748 A1    4/2010

* cited by examiner

*Primary Examiner* — Nikita Wells
(74) *Attorney, Agent, or Firm* — Browdy and Neimark, PLLC

(57) ABSTRACT

An appliance for disinfecting hand-held devices each having a surface that is contacted manually when the device is in use, composed of: a source of disinfecting radiation; and a conveyer system operative to convey the devices past the source with the top and/or bottom surfaces of each device facing the source, wherein the conveyor system is composed of a plurality of hollow, transparent rollers; and the source of disinfecting radiation includes a plurality of lamps, each housed in a respective one of the transparent rollers.

12 Claims, 14 Drawing Sheets

APPLIANCE FOR DISINFECTING HAND-HELD DEVICES

BACKGROUND OF THE INVENTION

The present invention is directed to an appliance for disinfecting hand-held devices having surfaces that are contacted manually when the device is in use Even in the cleanest environments, many kinds of microbes will begin to multiply on surfaces and sometimes reach harmful levels. If these contaminated surfaces are touched by individuals or contact everyday products, the transfer of microbes begins, resulting in cross-contamination. Pathogen bacteria, such as *Staphylococcus aureus*, including methicillin resistant *staphylococcus aureus* (MRSA) and *Escherichia Coli*, can be spread via cross-contamination, leading to infection and illness.

The increased use of cell phones, pdas, tablets, and other hand-held devices by patients, visitors and healthcare workers in healthcare facilities suggests the need to disinfect and prevent pathogen growth on these devices to reduce cross-contamination and possibly the incidence of hospital acquired infections.

BRIEF SUMMARY OF THE INVENTION

The present invention provides a disinfection appliance based on UV type light having an appropriate wavelength for disinfecting hand-held devices.

The invention also provides a protective film with antimicrobial capabilities that will cover the device screen, and possibly the device keys and back, to prevent, or at least impede, bacterial growth after the UV exposure.

One embodiment of the disinfection appliance according to the invention includes a conveyor system, which may be roller-based, for conveying devices along a conveying path, and lamps disposed along the conveying path for producing disinfecting light. The light wavelengths that presently appear to be most effective are those that produce UV type C light.

According to preferred embodiments of the invention, at least some of the rollers are transparent tubes, preferably of quartz, but also possibly of glass or plastic, each enclosing a UV lamp inside. Only the rollers enclosing a UV lamp need be transparent to UV radiation.

Alternatively, lamps that are disposed below the conveying path may be interposed between rollers in addition to, or in place of, lamps that are enclosed by transparent rollers. However, if the lamps are in rollers and the rollers are disposed next to one another, a higher light flux can be produced along a conveying path of limited length.

It is presently preferred to provide lamps both above and below the conveying path. However, useful embodiments of the invention can be provided with lamps that are only above, or only below, the conveying path.

Various embodiments of the invention can be employed to disinfect food trays that are used by people and that are used in production of animal feed, silverware, shoes, toys and produce.

The invention can also be used to decontaminate toxic, or suspected toxic, substances, such as white powder of unknown origin, which could be anthrax, or to decontaminate clothing.

Protective films according to the invention have a titanium dioxide or silver coating that shows bacteriostatic capabilities when exposed to light. Depending on the exposure time in the disinfecting appliance and the nature of the contaminating organism, some level of contamination reduction can be achieved by such a film as well. Microbiological reduction in any system is achieved by the UV dose: $C \times T$, where C is radiation concentration, in this case UV irradiance, and T is time. The higher the exposure time the higher the UV dose.

The film may be made of PET, polypropylene or similar materials such as urethane.

The film does not require an adhesive, although the use of an adhesive is a possibility.

One product that can be incorporated into the film surface and that also shows microbiocidal activity when exposed to normal light environments is sold under the trade name Oxititan, developed by Ecoactive Surfaces, Inc., a privately held Florida based company. According to the manufacturer, the ingredients of Oxititan are zinc, $TiO_2$ and, optionally, silicon dioxide in a colloid of water acting synergistically.

The film can also be made of a silver-containing material. One such product is a screen shield marketed by Seal Shield LLC, Jacksonville, Fla., under the trade designation ALIGN RIGHT™

Preliminary tests have shown that the film impregnated with Oxititan had some bacterial reduction capability. Therefore, incorporation into a $TiO_2$ film could have a beneficial effect.

Preferred embodiments of the disinfecting appliance according to the invention provide countertop conveyor systems constructed to disinfect handheld devices utilizing UV light. The system is constructed to achieve a disinfection end point of at least 3-log reduction, or 99.9%. The footprint of the appliance is dimensioned to accommodate at most 1 or 1½ tablet devices, so that the appliance can accommodate a tablet, such as an iPad®, and a cell phone at the same time. However, embodiments of the invention are not limited to any particular size.

One issue that is addressed, and successfully resolved, by the present invention is that the bottom faces of the devices to be disinfected will be in contact with the conveyor itself. If known conveyors were used, the result would be a shadow effect that would adversely affect the disinfection process of the surfaces in contact with the conveyor.

The rollers containing lamps may be surrounded by a highly reflective aluminum panel.

Compared to conventional belt systems, this approach has the benefits that it simplifies conveyor mechanics, reduces conveyor costs, allows 100% exposure of the bottom surfaces of devices to be treated, and reduces the appliance footprint due to the absence of shadowing effects.

Different mechanisms may be used to drive the rollers. One example may be a belt conveyor marketed by Mini-movers, Inc. This conveyor can be controlled with fixed or variable speed motors. The belt must be made of a material that provides enough grip for the rollers, including the quartz rollers.

For organisms, such as mold, that are more difficult to kill the initial number of lamps used may be 11, for example.

The system is designed in a way that the exposure time and the number of lamps can be adjusted in order to minimize the footprint, cost and the number of lamps. Exposure times can go from 20 to 60 seconds and each lamp may have an individual connector that can be connected or not, making the UV dose variable.

Preferred embodiments of appliances according to the invention may have a housing provided with a movable lid and equipped with mechanical and magnetic switches that operate in response to opening of the lid, a magnetic latch to lock the lid in its closed position, an ultrasonic sensor switch positioned and operative to detect introduction of a handheld device into the appliance, and connected to turn the conveying system and the lamps on when a device is detected, a high temperature switch to turn the appliance off if the internal temperature exceeds a selected value and a double curtain system that blocks escape of UV radiation from the appliance.

DETAILED DESCRIPTION OF THE INVENTION

Figure 1:
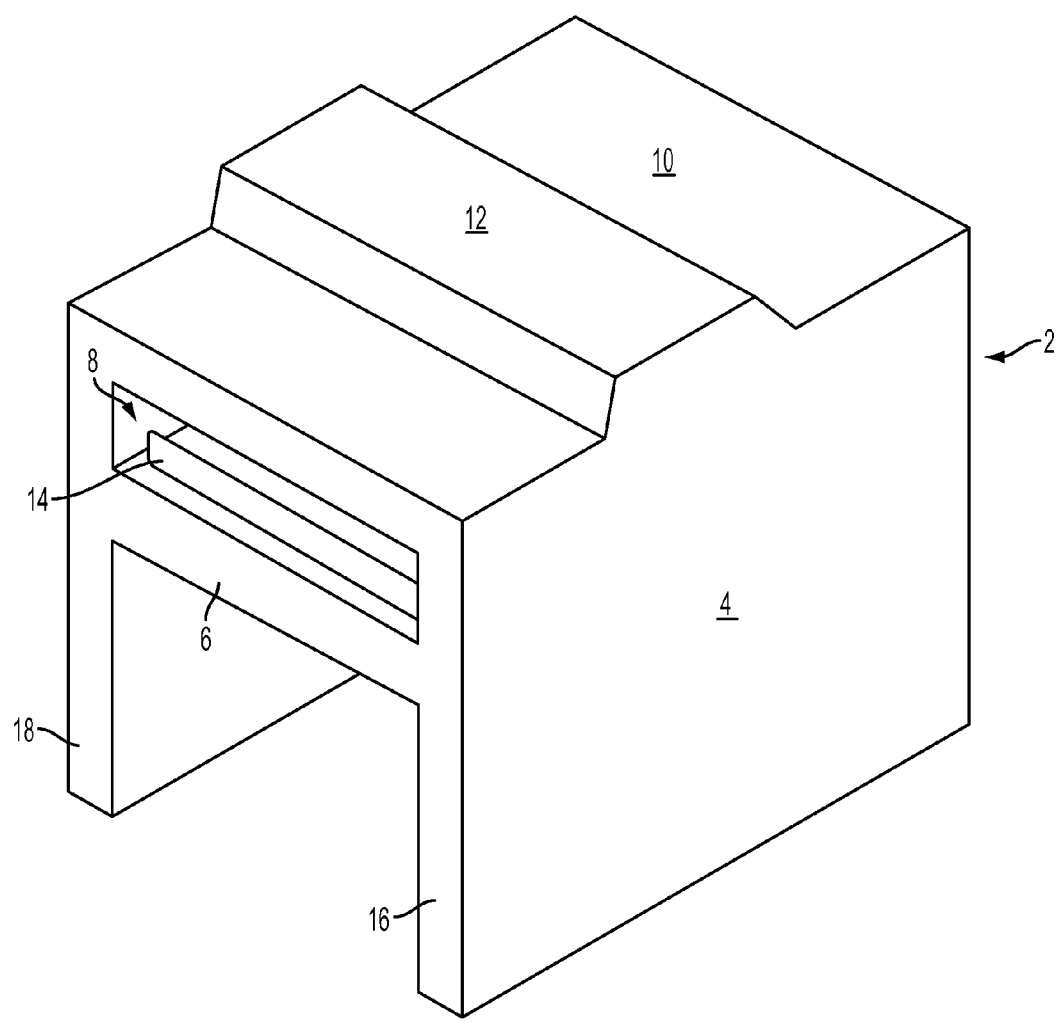
FIG. 1 is perspective view showing the housing of one embodiment of an appliance according to the invention.

FIG. 1 is a perspective view of one example of a housing 2 of an appliance according to the invention.

Housing 2 is composed of two vertical side walls, one of which is shown at 4, a front wall 6 provided with an entrance slot 8 for introduction of devices to be disinfected, and a rear wall (not shown) provided with an exit slot. The rear wall and exit slot are essentially identical to front wall 6 and entrance slot 8. The appliance also includes a top wall 10 provided to receive one or more UV disinfecting lamps 40. FIG. 1 also shows one roller 14 used to support and convey devices to be disinfected. The lower portions of side walls 4 are provided with legs 16, 18 for supporting the appliance while maintaining entrance 8 and the corresponding exit slot at a convenient height. While legs 16 and 18 are shown enclosing a hollow space that can extend along the entire length of appliance 2, the provision of such a hollow space is not required and the front and rear walls of the appliance could extend to the bottom of the appliance. In fact, FIG. 1 shows only one example of a housing, which can take many other forms, as will be apparent to those skilled in the art.

Figure 2:
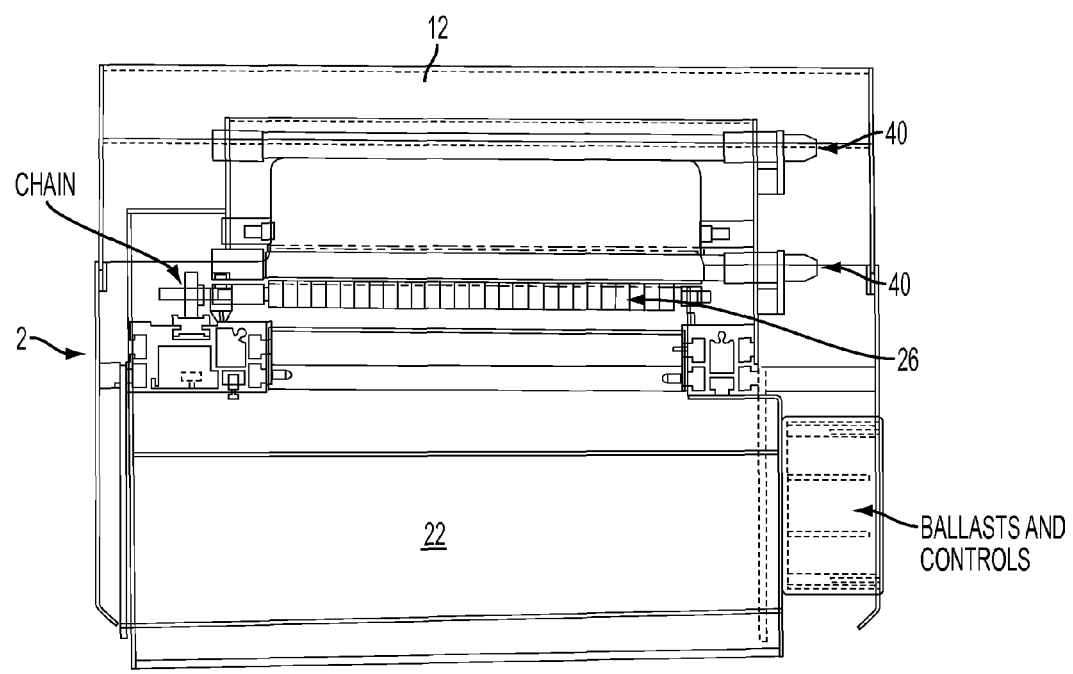
FIG. 2 is front elevational view of the appliance of FIG. 1 with the front of the housing removed.

FIG. 2 is a front elevational view of appliance 2 with the front wall removed.

Appliance 2 may be provided with an aluminum mounting structure 22 in the space between legs 16 and 18. The interior of housing 2 is provided with a plurality of UV lamps, including several lower lamps that will be located beneath the device being treated, and several upper lamps that are located above the space through which these devices pass. Housing 2 also contains a plurality of rollers, a number of which are hollow and transparent, each hollow and transparent roller surrounding, or housing a respective lower UV lamp. The rollers are coupled, at one or each end, to a drive system, such as chains, driven by a chain drive conveyer 26 that extends transversally across the space through which devices are conveyed. Chain drive conveyor 26 is rotated by a suitable drive device that may include a motor and drive gears (not shown in detail).

The interior of leg 16 may be provided with ballast and controls as shown in FIG. 2.

Figure 3:
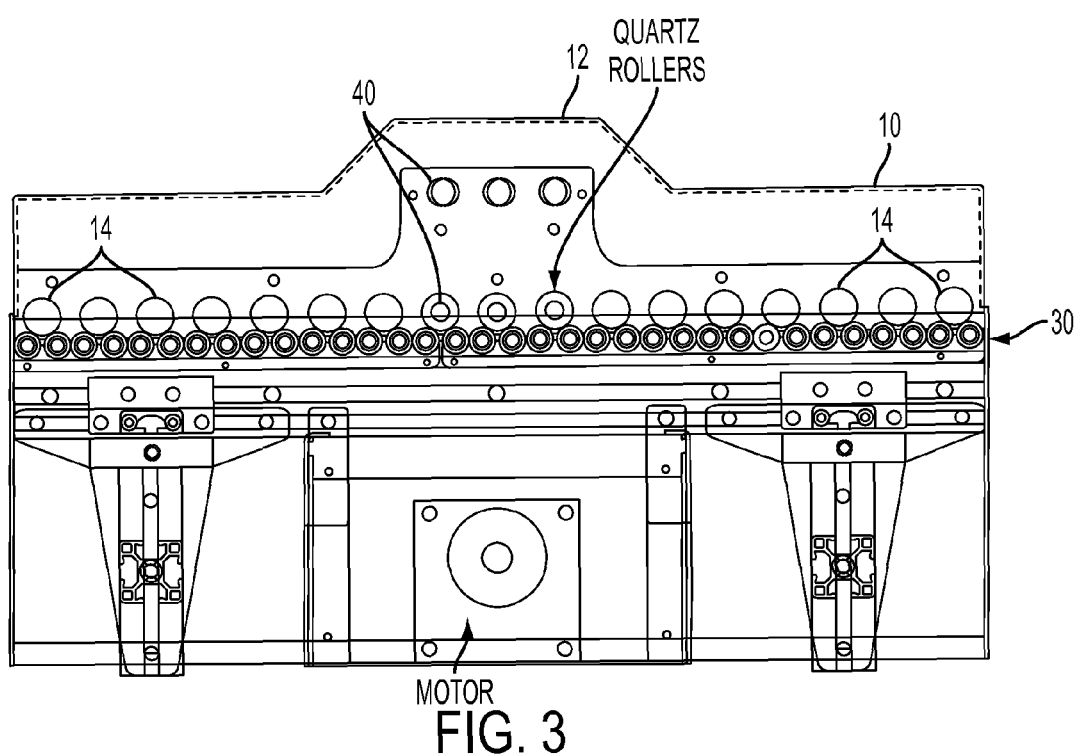
FIG. 3 is a side elevational view of the appliance of FIG. 1 with the side of the housing removed.

FIG. 3 is a side view of the appliance with a side wall 4 removed. As seen in FIG. 3, the interior of the appliance is provided with a device support arrangement in the form a plurality of rollers 14 that are supported on suitable bearings that engage a drive chain 30. Several of rollers 14, located midway between the entrance and exit slots of housing 2, are hollow and transparent, and may be made of quartz. While the rollers are mounted to rotate, the UV lamps are stationary.

An additional group of UV lamps is disposed in an upper portion of the appliance, beneath dome 12, to illuminate the upper surfaces of devices being treated.

Lamps having the model designation AAWHO/14T are presently considered to be suitable for achieving the desired results. For an exposure distance of 4 inches in the conveying direction, at least for the additional group of UV lamps disposed in the upper portion of the appliance, the total dosage per lamp will be approximately 50000 $\mu W/cm^2$. The lamps on the bottom can be less than one inch from the lower surfaces of the devices to be treated, since they are embedded in the rollers, and can provide a lower dosage level.

A drive chain 30 may be coupled to one end of each of the rollers, or two such drive chains can be provided at opposite ends of the rollers.

Figure 4:
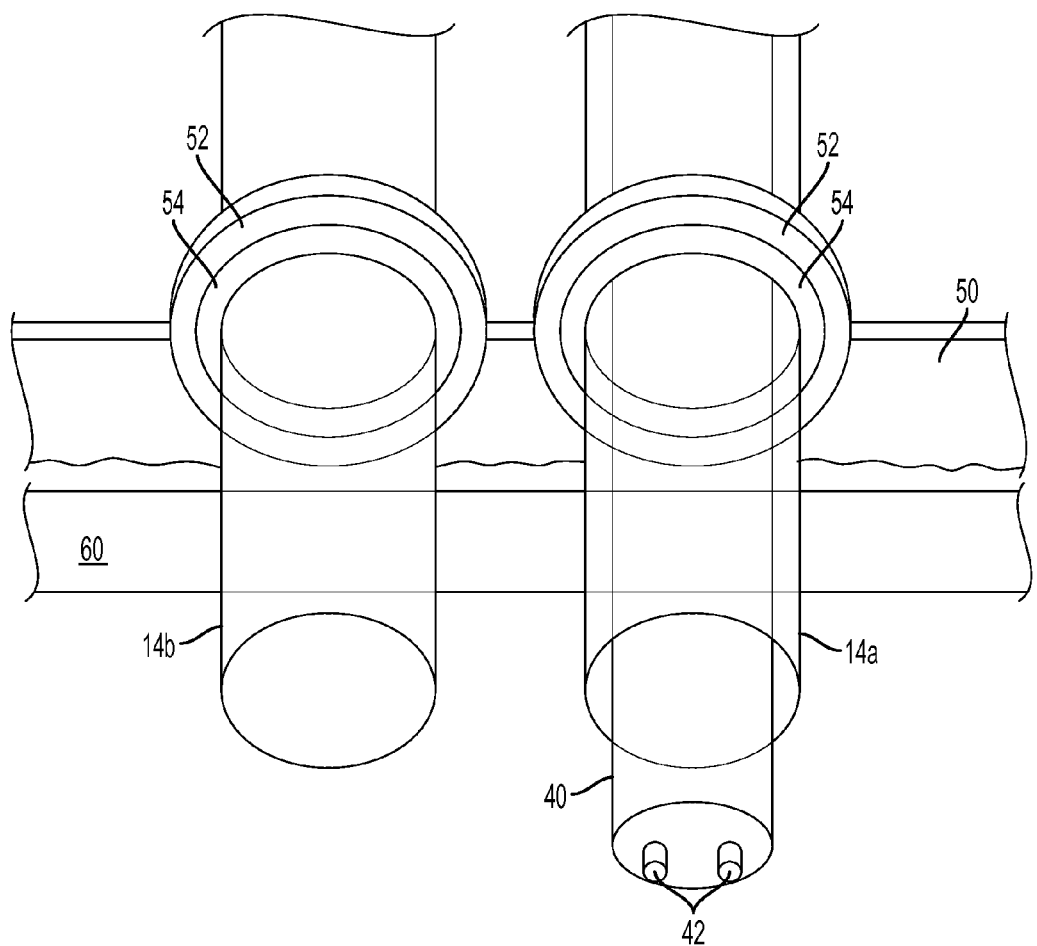
FIG. 4 is a detail perspective view of several components of the appliance.

FIG. 4 is a perspective detail view showing an end of two of the rollers 14a and 14b. Roller 14a is hollow and transparent and contains a UV lamp 40 having two current supply electrodes 42. Roller 14b may be solid and need not be transparent since it does not contain a lamp.

At each end, each of the rollers is supported in a vertical wall 50, optionally by a bearing arrangement that includes a stationary member 52 and a rotational member 54, which bearing arrangement may be in the form of a slide bearing or a roller bearing.

Rollers 14 engage a suitable drive structure such as chain 30, which is shown FIG. 3.

Lamps 40 may be supported at their ends by a separate stationary structure (not shown) constructed to allow electrical connections to be made to terminals 42.

According to a simple embodiment of the invention, as shown in FIG. 4, rollers 14 may be rotated by a simple drive belt 60 that travels beneath rollers 14 and directly contacts the surfaces of rollers 14. Preferably, drive belt 60 is made of a material having a relatively high coefficient of friction.

Figure 5:
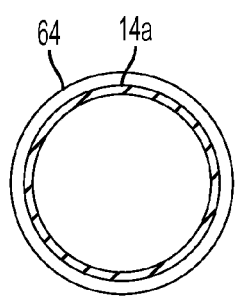
FIGS. 5, 6 and 7 are detail views of three embodiments of roller drive components according to the invention.

FIG. 5 shows an embodiment of a roller 14a provided, in the region of an associated drive belt, with a coating, or ring, 64 having a relatively high coefficient to friction.

Figure 6:
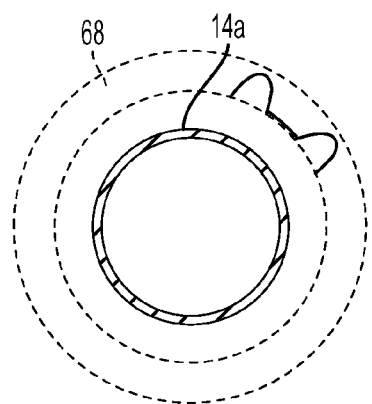

FIG. 6 shows an embodiment in which each roller 14 is secured to a toothed wheel, or gear wheel, 68 that will cooperate with a drive chain such as chain 30.

Figure 7:
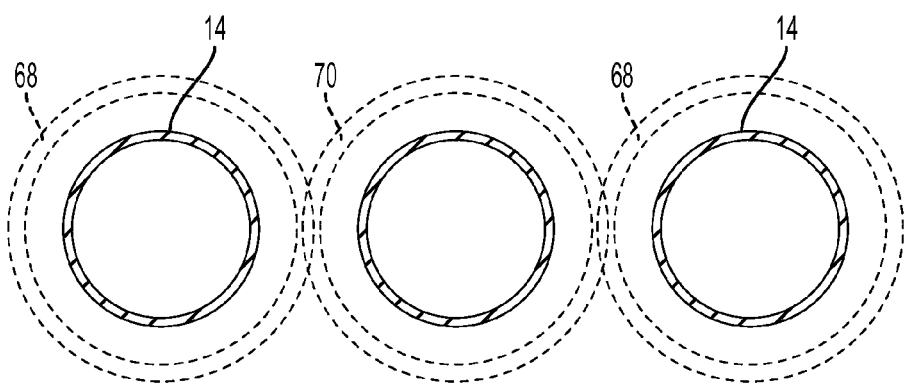
Figure 8:
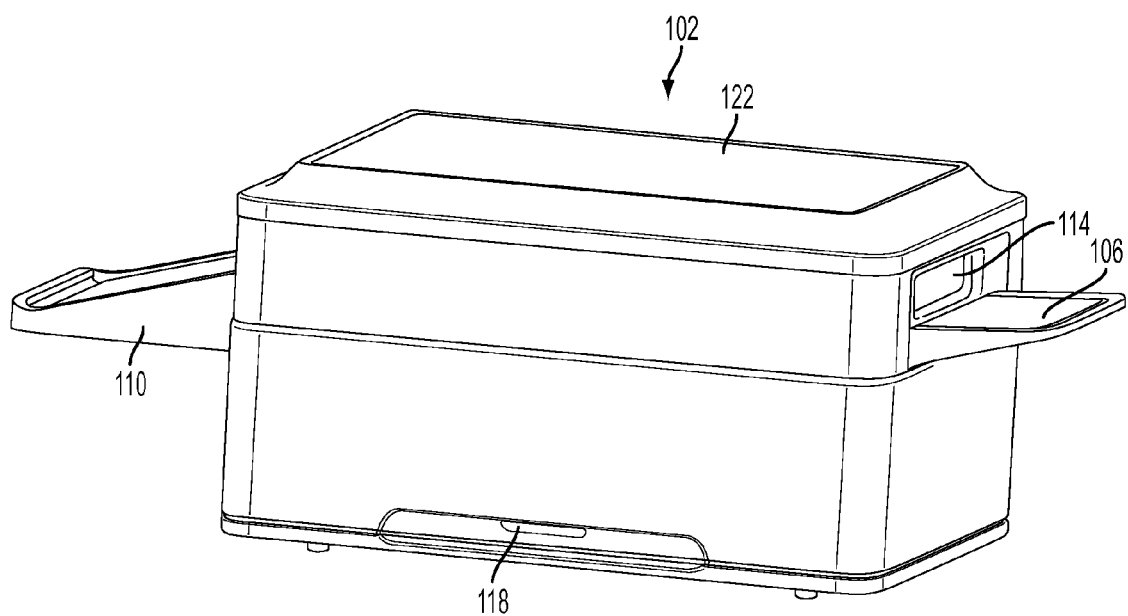
FIGS. 8-10 are perspective views of a further embodiment of the invention.
Figure 9:
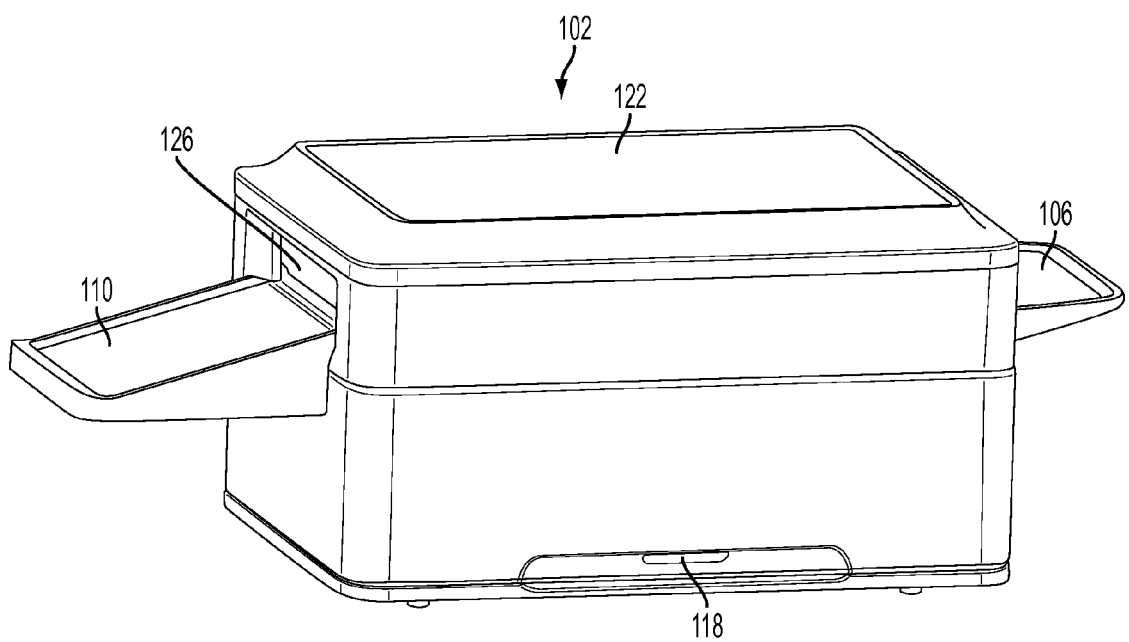
Figure 10:
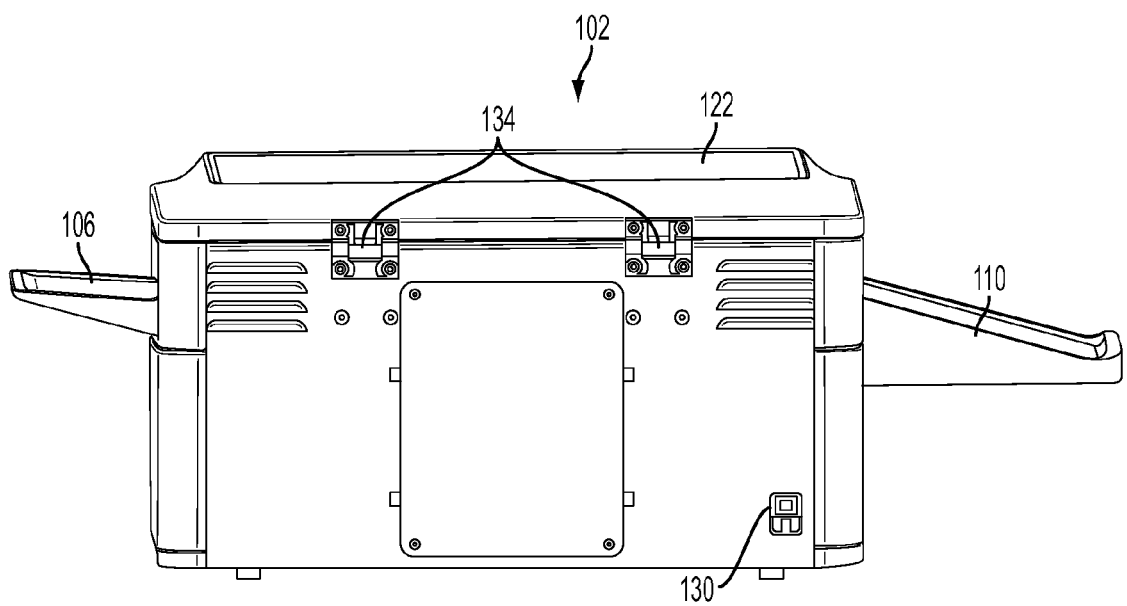

FIG. 7 shows an embodiment of the invention in which each transparent roller 14 (housing a lamp) is equipped with a toothed wheel 68, while further toothed wheels 70 are provided, each toothed wheel 70 being interposed between each succeeding pair of toothed wheels 68. According to this embodiment, conveyor 26 will engage one toothed wheel 68 or 70, at the entrance end of the appliance, and each toothed wheel 68, 70 will rotate the succeeding toothed wheel. With this arrangement, all of rollers 14 will be rotated in the same sense.

FIGS. 8-15 illustrate another embodiment of an appliance 102 according to the present invention. As shown particularly in FIGS. 8-10, appliance 102 is provided with an input tray 106, an output tray 110, an input opening 114 associated with input tray 106, a status indicator 118, a lid 122, an output opening 126 associated with output tray 110, a power switch 130 and lid hinges 134 connected between the body of appliance 102 and lid 122.

Status indicator 118 may be controlled to switch from red to blue before displaying green. The green color is an indication that the appliance is ready to be used.

The interior of appliance 102 is provided with a conveyor and lamps similar to those shown and described in connection with FIGS. 1-7.

Figure 11:
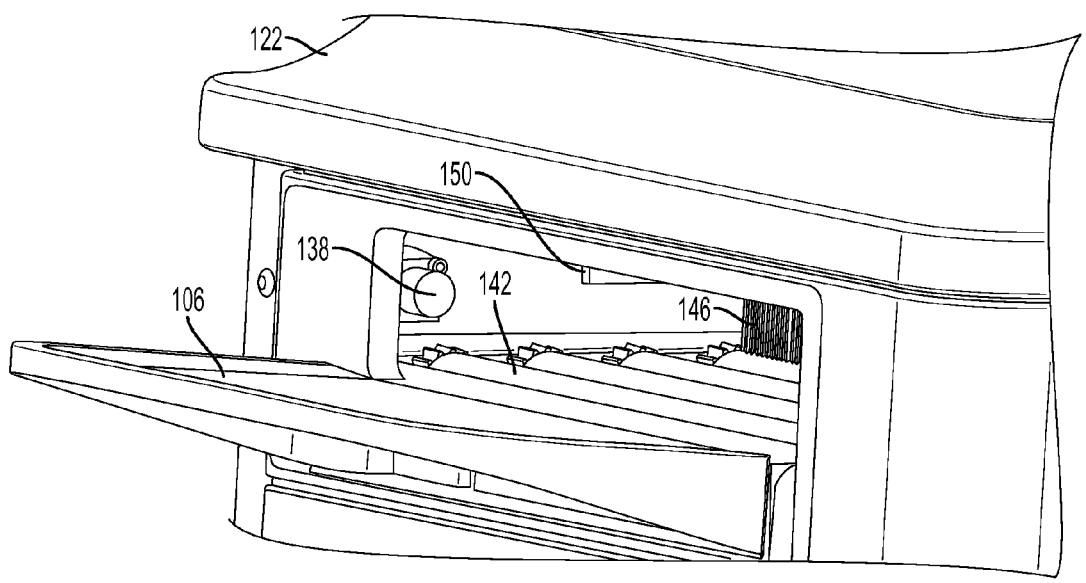
FIG. 11 is a perspective detail view of the input end of the further embodiment.

FIG. 11 shows a portion of the interior of appliance 102 at the input end. In one side wall of the appliance, there is provided an ultrasonic sensor, or detector, 138. Also shown in FIG. 11 is a portion of one UV blocking curtain 146, which may, according to one embodiment, be composed of a series of filaments, or strands, somewhat similar to the bristles of a paint brush. Blocking curtains 146 are located at least ahead of and behind the region provided with UV lamps, essentially at the center of the travel path for devices inside appliance 102.

The interior of appliance 102 may also be provided with a high temperature sensing switch 150 that is connected to turn the lamps off if the temperature within the conveying zone exceeds a selected value, for example 150° F. This will also cause status indicator 118 to turn red.

Figure 12:
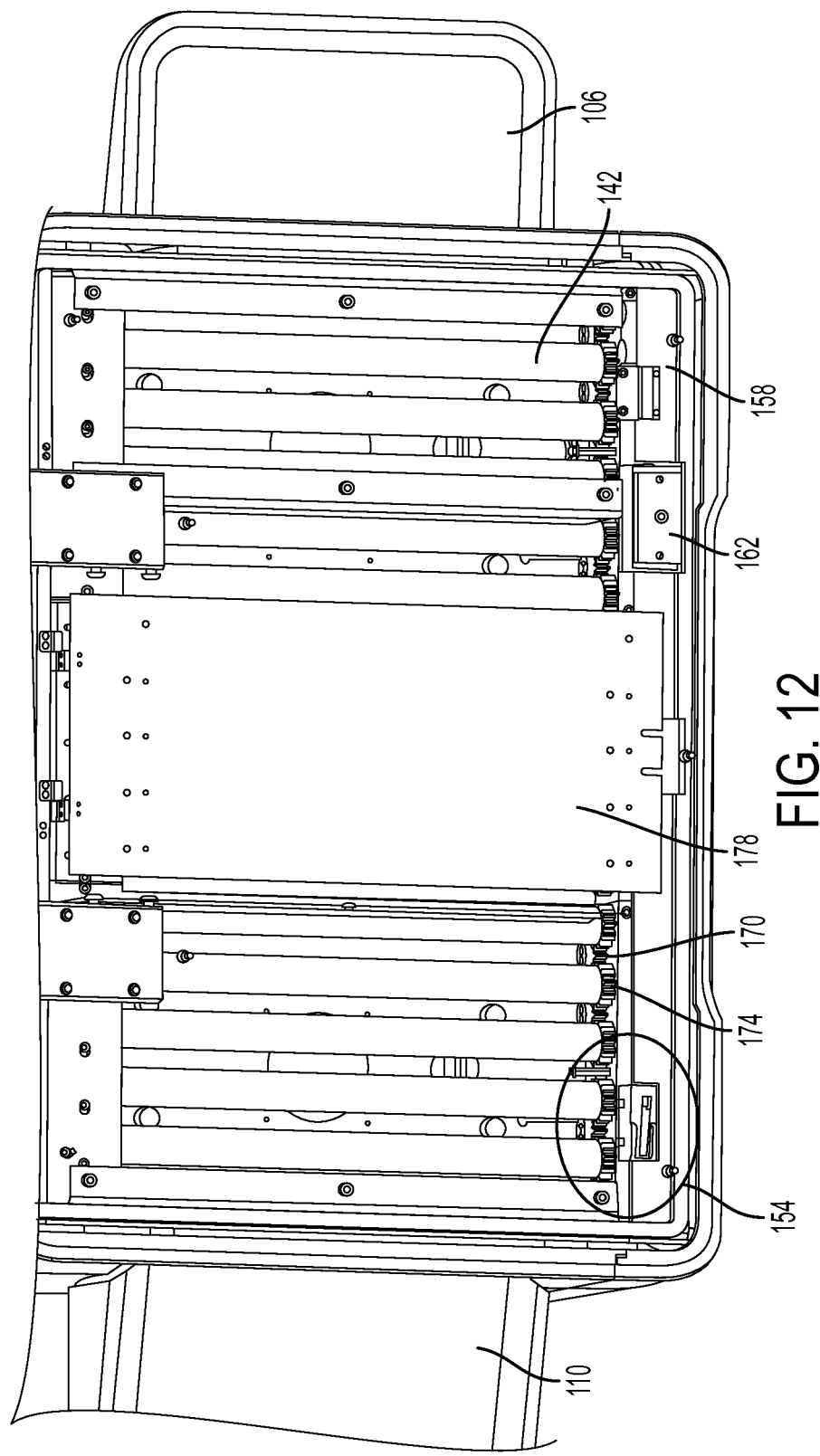
FIG. 12 is a top plan view of the further embodiment, with its lid removed.

FIG. 12 is a top plan view of the appliance with the lid open. At the top of the body of the appliance, which will interact with the edge of the lid that is remote from hinges 134, there are provided a mechanical safety switch 154, a magnetic safety switch 158 and a magnetic safety latch 162. As in the embodiment shown in FIGS. 1-3, the appliance is provided with a first group of UV lamps enclosed by transparent rollers to illuminate the bottoms of devices being treated, and a second plurality of UV lamps disposed above the path of travel of devices through the appliance. A plurality of UV blocking curtains 146 are disposed in the region between the first plurality and the second plurality of lamps.

Mechanical safety switch 154 is part of a three-level safety mechanism. This switch will interrupt power to the appliance control board as soon as top lid 122 is opened. This safety mechanism will prevent the user from being exposed to UV-C light.

Magnetic safety switch 158 is also part of the three-level safety mechanism. This switch will interrupt the DC power to relays on the control board of the appliance circuitry for supplying power to the UV relays as soon as lid 122 is opened. This safety mechanism will help to prevent the user from being exposed to UV-C light. The UV lamps cannot operate if the magnetic switch does not detect that lid 122 is closed.

Magnetic safety latch 162 is the third element of the three-level safety mechanism and latches lid 122 in the closed position with sufficient force to keep lid 122 closed. To open lid 122, the appliance has to be turned off in order to demagnetize latch 162.

Lid 122 will be held in position by magnetic latch 162

As can also be seen in FIG. 12, the conveying system for this embodiment is composed of a toothed belt 170 at one end of rollers 142. A second, identical, toothed belt may be associated with the opposite ends of the rollers. Each roller 142 is provided at one, or each, end with a toothed wheel 174, having the form shown in FIG. 6. The, or each, belt 170 is in toothed engagement with associated wheels 174 in order to rotate the rollers.

The center region of the travel path, where the lamps are located, is also provided with a separate top panel, or lid, 178, which are hinged to the upper surface of the body of appliance 102, below lid 122. The UV-C lamps above the path of travel for devices are carried by panel 178. Panel 178 can be pivoted open to facilitate replacement of the top lamps, or to remove a device that has been stopped in the UV module. The input region and the output region of the conveying path may each also be provided with one or more further lids.

Figure 13:
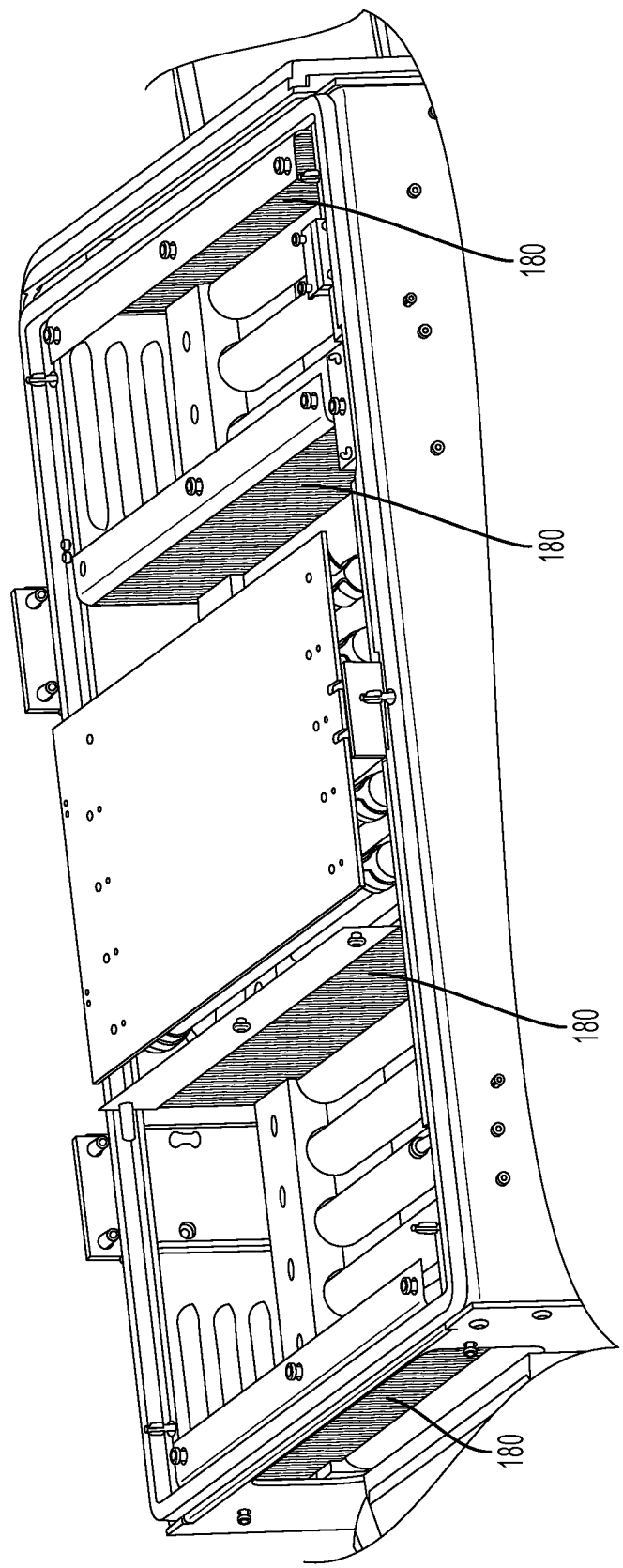
FIG. 13 is a perspective detail view of the further embodiment, showing UV blocking curtains.

FIG. 13 is a top perspective view of the appliance with lid 122 removed. The conveying region has a plurality of UV blocking curtains 180 to prevent the escape of UV radiation out of the appliance. Curtains 180 include at least one curtain at the input end, adjacent input opening 114, at least one curtain at the output end, adjacent output opening 126, at least one curtain ahead of, or upstream of, the UV lamps and at least one curtain following, or downstream of, the UV lamps, preferably immediately before and after the UV lamps.

The curtain at the input end is located to be fully closed when a device enters the UV section, and the device will not reach the curtain at the output end until after having left the UV section. The curtain arrangement will assure that only a minimum UV light, if any, can escape when a device is moving through the curtains and when there is no device in the appliance. The curtains are composed of strands of a material selected to block UV-C radiation and made of a suitable UV blocking material known in the art.

The conveyor system of an appliance according to the invention may be provided with three conveyor modules, or units, each having rollers driven by a separate motor. Although the conveyor system could be composed of a single conveyor module with a single motor, division of the conveyor system into three modules, each with its own motor, allows the use of smaller motors with lower torque requirements, facilitates manufacture by allowing higher tolerances, and facilitates repair and maintenance in the field.

Figure 14:
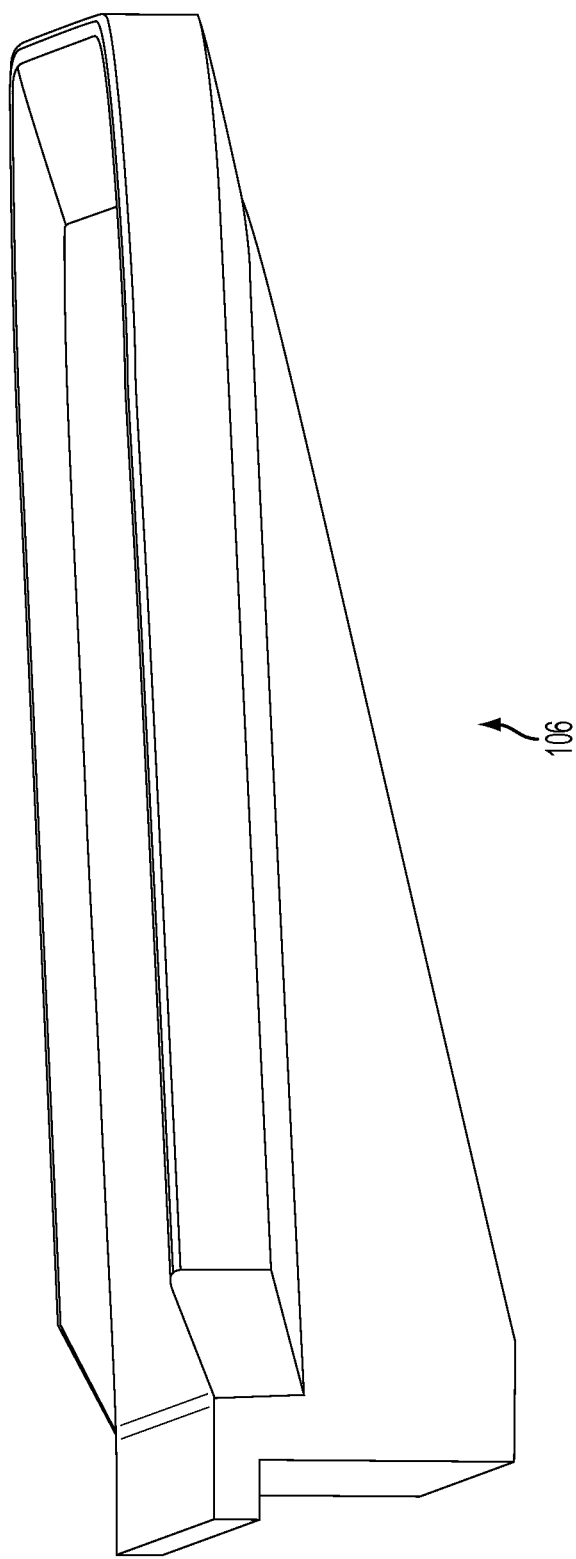
FIG. 14 is a pictorial view of an input tray used with the appliance.
Figure 15:
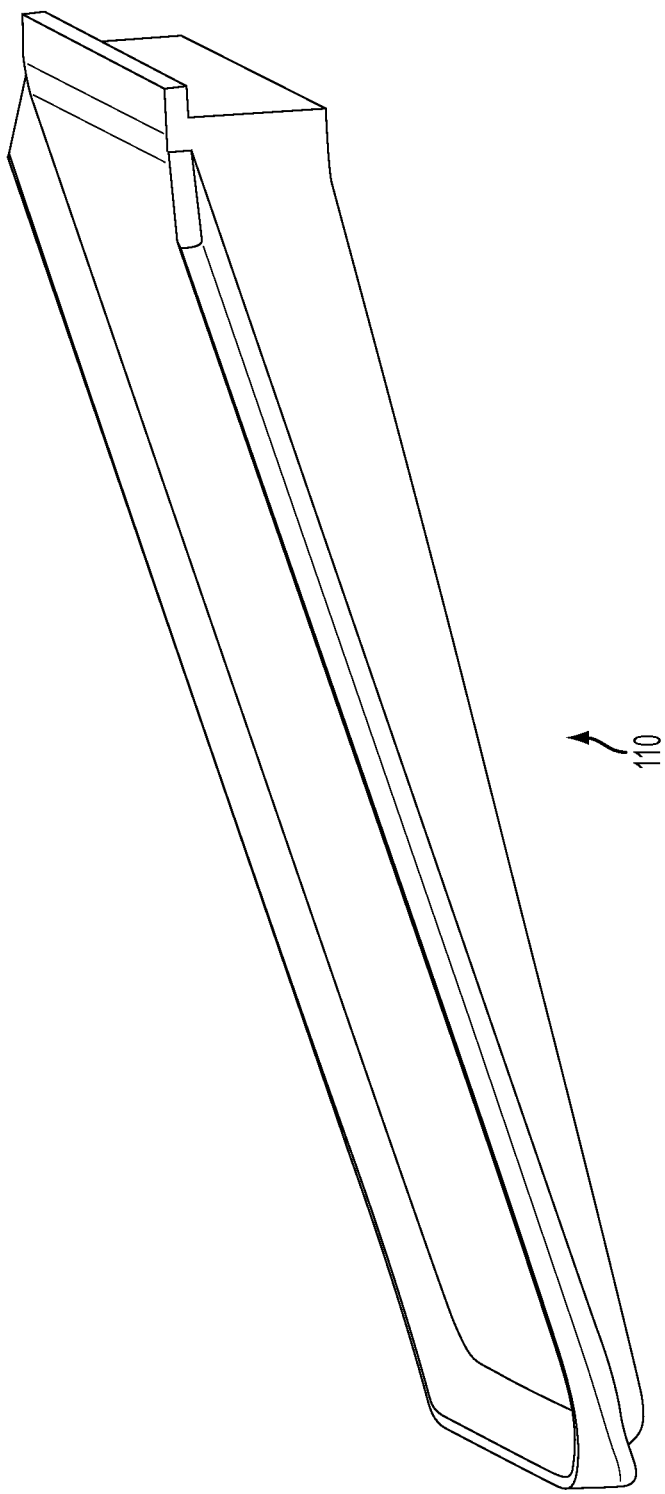
FIG. 15 is a pictorial view of an output tray used with the appliance.

Exemplary embodiments of input tray 106 and output tray 110 are shown in FIGS. 14 and 15, respectively. As can be seen in FIG. 14, input tray 106 slopes downwardly toward the input opening to allow devices to slide into the appliance. As can be seen in FIG. 15, output tray 110 slopes downwardly away from the output opening to allow treated devices to slide away from the appliance and is constructed with a raised lip at its free end to prevent devices from falling onto the floor after exiting the appliance.

Figure 16:
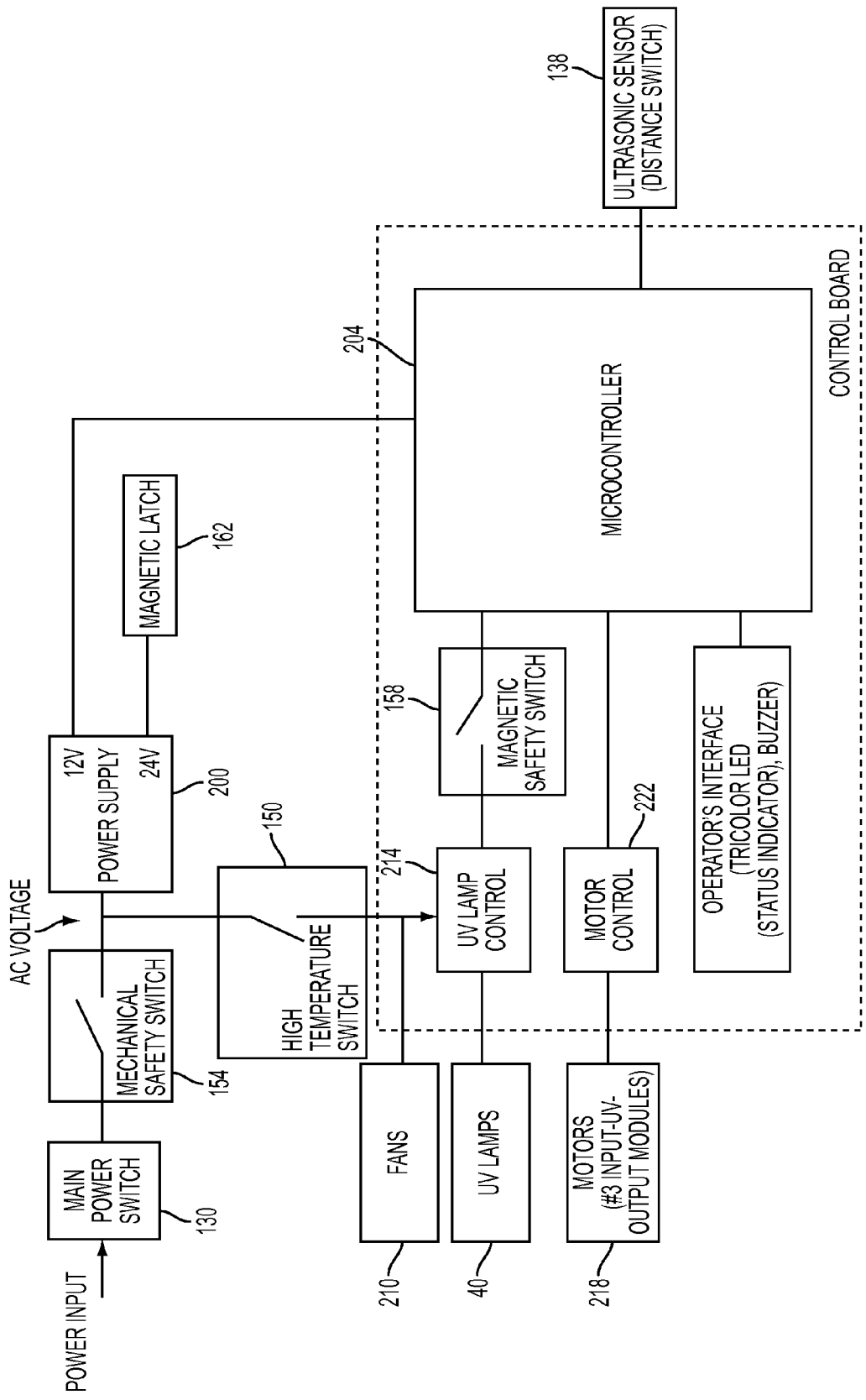
FIG. 16 is a block diagram showing the electrical components of the further embodiment.

FIG. 16 is a block diagram of one example of electrical circuitry that can be used to control the appliance according to the invention. As shown, operating power, such as from an electric outlet, is supplied to a main power switch 130 and from there to a mechanical safety switch 154, high temperature responsive switch 150 and a power supply that supplies 24 volt power to magnetic latch 162 and 12 volt power to a microcontroller 204. Ultrasonic detector 138 is also connected to microcontroller 204. Microcontroller 204 is also connected to an operator's interface, which includes status indicator 118.

Operating power is supplied through high temperature switch 150 to cooling fans 210 and lamp control 214. Operating power is supplied to lamps 40 from microcontroller 204 through switch 158 and a lamp control 214. Operating power is supplied to motors 218 from microcontroller 204 through a motor control 222.

Microcontroller 204 is constructed according to principles well known in the art to supply control signals to lamp control 214 and motor control 222, which supplies operating power for motors 218.

As can be seen, whenever any one of switches 150, 154 and 158 is open, the supply of operating power to lamps 40 is discontinued.

Microcontroller 204 is constructed to respond to a proximity signal from detector 138 to initiate operation of motors 218 and to cause operating power to be supplied to lamps 40. Fans 210 will continue to operate as long as switches 150 and 154 are closed. Lamps 40 will be turned off whenever magnetic safety switch 158 is open.

Small handheld devices, e.g., having a length or width smaller than 3 inches, may be introduced into the appliance on a simple transparent quartz tray (not shown) of conventional form.

The conveyor system according to the invention is divided into three independently driven sections, or modules, a) input, b) UV and c) output.

The input module receives a device to be sanitized and conveys it to the UV Module. There are, for example, six rollers in the input module and they are preferably made of acrylic.

The UV module is where the actual sanitizing process takes place. This module has, for example, five quartz rollers within each of which each there is housed a UV-C lamp 40. Since quartz allows UV-C to pass through it, the bottom surface of a conveyed device will have full exposure without any shadows. Also in this module, there are, for example, five lamps 40 on top, above the devices being treated, to allow the top surfaces of the devices to be exposed to UV-C as well. Surfaces below the bottom lamps and above the top lamps are made of, coated with, or provided with a layer of, a reflective material, e.g., aluminum, with a mirror finish to allow UV-C to be reflected, thus increasing the efficiency of radiation utilization.

A handheld device to be sanitized will be introduced from inlet tray 106 into input opening 114. Ultrasonic distance, or proximity, sensing switch 138 will detect entry of the handheld device into the appliance and turn on the operating mechanisms of the roller based conveyor and the UV-C lamps. Status indicator 118 may be operated to turn purple, indicating that the UV-C lamps are turned on. Then, the device will be conveyed on rollers 142 through the UV lamp zone and delivered to output opening 126. At any time, a new device can be introduced into the appliance before the device that was previously introduced exits the conveying path.

At a preset time, for example 35 seconds, after the last detection of a device by ultrasonic sensor 138, the roller based conveyor and the UV-C lamps will be turned off. At that time, status indicator 118 may be caused to turn green.

Once a conveyed device exits the UV module, it will be conveyed to the output module, which will in turn move it to output opening 126 and then onto tray 110.

The output module is identical to the input module in construction.

The main operations of the appliance are controlled by a microprocessor based control board.

The following functions are controlled with software in the control board:

Response to detection of a device by sensor switch 138;
Operation of the conveyor modules;
Operation of UV-C lamps 40 (FIG. 3);
Operation of the status indicator;
Operation of the ballast feedback for proper lamp operation;
Monitoring of the number of cycles run.

Operation of the following components are controlled by hardware and are not dependent on software: mechanical switch 154; magnetic switch 158; magnetic latch 162; and high temperature switch 150.

Prototype testing has indicated that most of the sleeves and rollers may not need bearings to rotate, and can simply be supported in openings or recesses in vertical support walls. In this case, it would be desirable to select support walls of materials having a low coefficient of friction. This approach allows the rollers/sleeves to be mounted very close to each other. Each roller/sleeve may be provided with a tape band having a high coefficient of friction to engage with the drive belt and to compensate for slight differences in roller vertical positioning.

Several tests, reported below, were performed to measure the effects of UV light on test objects that include slide mailers, which simulate the cell phone backs and keypads, and petri dish outer surfaces, which simulate tablet and cell phone screens. The results of those tests appear below.

Note: One hundred microliters of the initially prepared *Staphylococcus aureus, Klebsiella pneumonia; Bacillus stearothermophilus* suspension was added to the top and bottom outer surfaces of slide mailers, spread over a 2"×2" surface, and allowed to air dry before UV exposure. Slide mailers are plastic pieces that simulate cell phone backs and keys. Heat inactivated horse serum was added at a 5% concentration to *Staphylococcus aureus* (SA) bacterial suspensions for samples listed as "with serum". Bacteria were harvested from both top and bottom surfaces of mailers using sterile dacron swabs moistened with sterile reagent grade water (1 ml in tube). Each swab was immediately vortexed in the remainder of corresponding 1 ml water tubes and plated on tryptic soy agar to obtain plate counts.

| Sample Number/Sample Site | Sample Type/ Media Type | Test Code Limit of Sensitivity | Bacterial Count: Heterotrophic Plate Count |
|---|---|---|---|
| Sa + 5T-S.a. 5% Serum 5 Lamps Top | Swab- Aerobic TSA | 10 CFU/swab B004 | None Detected |
| Sa + 5B-S.a. 5% Serum 5 Lamps Bottom | Swab- Aerobic TSA | 10 CFU/swab B004 | None Detected |
| Kp + 5T-K.p. 5% Serum 5 Lamps Top | Swab- Aerobic TSA | 10 CFU/swab B004 | None Detected |
| Kp + 5B-K.p. 5% Serum 5 Lamps Bottom | Swab- Aerobic TSA | 10 CFU/swab B004 | None Detected |
| Bs + 5T-B.s. 5% Serum 5 Lamps Top | Swab- Aerobic TSA | 10 CFU/swab B004 | None Detected |
| Bs + 5B-B.s. 5% Serum 5 Lamps Bottom | Swab- Aerobic TSA | 10 CFU/swab B004 | None Detected |
| Bs + C-B.s. Control 5% Serum | Swab- Aerobic TSA | 10 CFU/swab B004 | 200,000 |
| Sa – C-S.a. Control No Serum | Swab- Aerobic TSA | 10 CFU/swab B004 | 20,000 |
| Sa + C-S.a. Control 5% Serum | Swab- Aerobic TSA | 10 CFU/swab B004 | 20,000 |
| Kp – C-K.p. Control No Serum | Swab- Aerobic TSA | 10 CFU/swab B004 | 21,000 |
| Kp + C-K.p. Control 5% Serum | Swab- Aerobic TSA | 10 CFU/swab B004 | 20,000 |
| Sa-3T-S.a. No Serum 3 Lamps Top | Swab- Aerobic | 10 CFU/swab B004 | None Detected |
| Sa-3B-S.a. No Serum 3 Lamps Bottom | Swab- Aerobic | 10 CFU/swab B004 | None Detected |
| Sa + 3T-S.a. 5% Serum 3 Lamps Top | Swab- Aerobic | 10 CFU/swab B004 | None Detected |
| Sa + 3B-S.a. 5% Serum 3 Lamps Bottom | Swab- Aerobic | 10 CFU/swab B004 | None Detected |
| Ka-3T-K.p. No Serum 3 Lamps Top | Swab- Aerobic | 10 CFU/swab B004 | None Detected |
| Ka-3B-K.p. No Serum 3 Lamps Bottom | Swab- Aerobic | 10 CFU/swab B004 | None Detected |
| Ka + 3T-K.p. 5% Serum 3 Lamps Top | Swab- Aerobic | 10 CFU/swab B004 | None Detected |
| Ka + 3B-K.p. 5% Serum 3 Lamps Bottom | Swab- Aerobic | 10 CFU/swab B004 | None Detected |
| B.s. + 3T-B.s. 5% Serum 3 Lamps Top | Swab- Aerobic | 10 CFU/swab B004 | 30 |

-continued

| Sample Number/Sample Site | Sample Type/ Media Type | Test Code Limit of Sensitivity | Bacterial Count: Heterotrophic Plate Count |
|---|---|---|---|
| B.s. + 3B-B.s. 5% Serum 3 Lamps Bottom | Swab-Aerobic | 10 CFU/swab B004 | 10 |

Note:
S.a. = *Staphylococcus aureus*;
K.p. = *Klebsiella pneumonia*;
B.s. = *Bacillus stearothermophilus*;
5T = 5 lamps above test objects;
5B = 5 lamps below test object;
3T = 3 lamps above test objects;
3B = 3 lamps below test object;
+C = with serum;
−C = without serum;
CFU = Colony Forming Units;
B004 = the laboratory's test report code for direct surface swabs-aerobes
EI14314

Note: One hundred microliters of the initially prepared *Staphylococcus aureus* bacteria suspension (95,000,000 CFU/ml) was added to the top and bottom of slide mailer outer surfaces, spread over a 2"×2" surface, and allowed to air dry before UV exposure.

Heat inactivated horse serum was added at a 5% concentration to *Staphylococcus aureus* (SA) bacterial suspensions for samples listed as "with serum". Bacteria were harvested from both top and bottom surfaces of mailers using sterile dacron swabs moistened with sterile reagent grade water (1 ml in tube). Each swab was immediately vortexed in the remainder of corresponding 1 ml water tubes and plated on tryptic soy agar to obtain plate counts. Samples were plated in triplicate: A, B, C.

| Sample Number/ Sample Site | Sample Type/ Media Type | Test Code Limit of Sensitivity | Bacterial Count: Heterotrophic Plate Count |
|---|---|---|---|
| *Staphylococcus aureus*-Mailer A-Control with Serum | Swab-Aerobic TSA | 10 CFU/swab B004 | 235000 |
| *Staphylococcus aureus*-Mailer B-Control with Serum | Swab-Aerobic TSA | 10 CFU/swab B004 | 210000 |
| *Staphylococcus aureus*-Mailer C-Control without Serum | Swab-Aerobic TSA | 10 CFU/swab B004 | 76000 |
| SA A-Mailer-UV-No Serum - Top | Swab-Aerobic TSA | 10 CFU/swab B004 | None Detected |
| SA A-Mailer-UV-No Serum-Bottom | Swab-Aerobic TSA | 10 CFU/swab B004 | None Detected |
| SA B-Mailer-UV-No Serum-Top | Swab-Aerobic TSA | 10 CFU/swab B004 | None Detected |
| SA B-Mailer-UV-No Serum-Bottom | Swab-Aerobic TSA | 10 CFU/swab B004 | None Detected |

EI14443

Note: One hundred microliters of the initially prepared *Staphylococcus aureus* bacteria suspension (95,000,000 CFU/ml) was added to the top and bottom of petri dish (inanimate, non-food contact surfaces that simulate the screens of tablets, cell phones, etc.) outer surfaces, spread over a 2"×2" surface, and allowed to air dry before UV exposure. Heat inactivated horse serum was added at a 5% concentration to *Staphylococcus aureus* (SA) bacterial suspensions for samples listed as "with serum". Bacteria were harvested from both top and bottom surfaces of dishes using sterile dacron swabs moistened with sterile reagent grade water (1 ml in tube). Each swab was immediately vortexed in the remainder of corresponding 1 ml water tubes and plated on tryptic soy agar to obtain plate counts. Samples were plated in triplicate: A, B, C.

| Sample Number/ Sample Site | Sample Type/ Media Type | Test Code Limit of Sensitivity | Bacterial Count: Heterotrophic Plate Count |
|---|---|---|---|
| *Staphylococcus aureus*-Dish A-Control with Serum | Swab-Aerobic TSA | 10 CFU/swab B004 | 650000 |
| *Staphylococcus aureus*-Dish B-Control with Serum | Swab-Aerobic TSA | 10 CFU/swab B004 | 750000 |
| *Staphylococcus aureus*-Dish C-Control without Serum | Swab-Aerobic TSA | 10 CFU/swab B004 | 240000 |
| SA A-Petri Dish UV-No Serum-Top | Swab-Aerobic TSA | 10 CFU/swab B004 | None Detected |
| SA A-Petri Dish-UV-No Serum-Bottom | Swab-Aerobic TSA | 10 CFU/swab B004 | None Detected |
| SA B-Petri Dish-UV-No Serum-Top | Swab-Aerobic TSA | 10 CFU/swab B004 | None Detected |
| SA B-Petri Dish-UV-No Serum-Bottom | Swab-Aerobic TSA | 10 CFU/swab B004 | None Detected |

EI14444

Note: Top and bottom surfaces of petri dishes (inanimate, non-food contact surfaces) were challenged with *Staphylococcus aureus* and *Klebsiella pneumoniae* bacteria in triplicate to determine the efficacy of UV exposure generated by the experimental test unit. EPA Guidelines, DIS/TSS-10, were followed. In summary, ten microliters of 18 hour bacteria broth cultures were added to 1×1 inch square areas on both top and bottom petri dish test surfaces. Both bacteria challenges were performed independently. A sterile wooden stick was used to spread each test inoculum prepared with an organic load (5% heat-inactivated serum) over 1×1 inch square test areas and allowed to dry for 40 minutes in a bacteriological incubator at 35 degrees Celsius. Test bacteria were recovered using sterile water diluent and dacron swabs. Heterotrophic plate counts were obtained using trypticase soy agar (TSA). The number of viable bacteria on each test surface after drying, with and without UV exposure, allowed bacterial reductions to be determined and compared to the expected 99.9% performance requirement. Abbreviations: SA=*Staphylococcus aureus*, KP=*Klebsiella pneumoniae*.

| Sample Number/Sample Site | Sample Type/ Media Type | Test Code Limit of Sensitivity | Bacterial Count: Heterotrophic Plate Count |
|---|---|---|---|
| 1-SA A-Petri Dish-UV-Serum-Top | Swab-Aerobic | 10 CFU/swab B004 | None Detected |
| 2-SA A-Petri Dish-UV-Serum-Bottom | Swab-Aerobic | 10 CFU/swab B004 | None Detected |

| Sample Number/Sample Site | Sample Type/Media Type | Test Code Limit of Sensitivity | Bacterial Count: Heterotrophic Plate Count |
|---|---|---|---|
| 3-SA B-Petri Dish-UV-Serum-Top | Swab-Aerobic | 10 CFU/swab B004 | None Detected |
| 4-SA B-Petri Dish-UV-Serum-Bottom | Swab-Aerobic | 10 CFU/swab B004 | None Detected |
| 5-SA C-Petri Dish-UV-Serum-Top | Swab-Aerobic | 10 CFU/swab B004 | None Detected |
| 6-SA C-Petri Dish-UV-Serum-Bottom | Swab-Aerobic | 10 CFU/swab B004 | None Detected |
| 7-SA A-Petri Dish-No UV-Serum-Top | Swab-Aerobic | 10 CFU/swab B004 | 11,200,000 |
| 8-SA A-Petri Dish-No UV-Serum-Bottom | Swab-Aerobic | 10 CFU/swab B004 | 10,900,000 |
| 9-SA B-Petri Dish-No UV-Serum-Top | Swab-Aerobic | 10 CFU/swab B004 | 14,100,000 |
| 10-SA B-Petri Dish-No UV-Serum-Bottom | Swab-Aerobic | 10 CFU/swab B004 | 12,800,000 |
| 11-SA C-Petri Dish-No UV-Serum-Top | Swab-Aerobic | 10 CFU/swab B004 | 8,900,000 |
| 12-SA C-Petri Dish-No UV-Serum-Bottom | Swab-Aerobic | 10 CFU/swab B004 | 10,500,000 |
| 14-KP A-Petri Dish-UV-Serum-Top | Swab-Aerobic | 10 CFU/swab B004 | None Detected |
| 15-KP A-Petri Dish-UV-Serum-Bottom | Swab-Aerobic | 10 CFU/swab B004 | None Detected |
| 16-KP B-Petri Dish-UV-Serum-Top | Swab-Aerobic | 10 CFU/swab B004 | None Detected |
| 17-KP B-Petri Dish-UV-Serum-Bottom | Swab-Aerobic | 10 CFU/swab B004 | None Detected |
| 18-KP C-Petri Dish-UV-Serum-Top | Swab-Aerobic | 10 CFU/swab B004 | None Detected |
| 19-KP C-Petri Dish-UV-Serum-Bottom | Swab-Aerobic | 10 CFU/swab B004 | None Detected |
| 20-KP A-Petri Dish-No UV-Serum-Top | Swab-Aerobic | 10 CFU/swab B004 | 870,000 |
| 21-KP A-Petri Dish-No UV-Serum-Bottom | Swab-Aerobic | 10 CFU/swab B004 | 990,000 |
| 22-KP B-Petri Dish-No UV-Serum-Top | Swab-Aerobic | 10 CFU/swab B004 | 1,230,000 |
| 23-KP B-Petri Dish-No UV-Serum-Bottom | Swab-Aerobic | 10 CFU/swab B004 | 1,100,000 |
| 24-KP C-Petri Dish-No UV-Serum-Top | Swab-Aerobic | 10 CFU/swab B004 | 840,000 |
| 25-KP C-Petri Dish-No UV-Serum-Bottom | Swab-Aerobic | 10 CFU/swab B004 | 280,000 |

EI14471

Several tests were also performed to measure the effects of UV light on a protective film used in the invention. The results of those tests are reproduced below.

| | | | | | | |
|---|---|---|---|---|---|---|
| | | | Film tests | | | |
| | | | Study ID NG3263 | | | |
| Test Microorganism | Sample | Time Point | CFU/Sample | Average CFU/Sample | R Value (Log10 Reduction) | Percent Reduction |
| S. aureus ATCC 6538 | Control | Time Zero | 2.70E+05 | 2.98E+05 | N/A | |
| | | Time Zero | 3.25E+05 | | | |
| | | 24 Hour | 3.42E+05 | 2.57E+05 | | |
| | | 24 Hour | 1.72E+05 | | | |
| | Silver Treated | 24 Hour | <5 | <5 | 4.41 | >99.99% |
| | | 24 Hour | <5 | | 4.41 | >99.99% |
| E. coli ATCC 8739 | Control | Time Zero | 1.15E+05 | 1.20E+05 | N/A | |
| | | Time Zero | 1.50E+05 | | | |
| | | Time Zero | 9.50E+04 | | | |
| | | 24 Hour | 1.48E+07 | 1.51E+07 | | |
| | | 24 Hour | 1.84E+07 | | | |
| | | 24 Hour | 1.20E+07 | | | |
| | Silver Treated | 24 Hour | <5 | <5 | 6.48 | >99.9999% |
| | | 24 Hour | <5 | | 6.48 | >99.9999% |
| | | 24 Hour | <5 | | 6.48 | >99.9999% |

| | | | | | |
|---|---|---|---|---|---|
| | | | Study ID NG3264 | | |
| Sample | Time Point | CFU/Sample | R Value (Log10 Reduction) Compared to Control at each Time Point | Percent Reduction | R Value (Log10 Reduction) Compared to Time Zero Control | Percent Reduction |
| Control | Time Zero | 1.95E+05 | N/A | | N/A | |
| | 2 Hour | 8.40E+04 | | | | |
| | 4 Hour | 3.80E+03 | | | | |
| | 6 Hour | 6.95E+03 | | | | |

-continued

| | | Film tests | | | |
|---|---|---|---|---|---|
| Oxititan | 2 Hour | 3.25E+04 | 0.41 | 61.31% | 0.78 | 83.33% |
| Treated | 4 Hour | 2.65E+03 | 0.16 | 30.26% | 1.87 | 98.64% |
| | 6 Hour | 2.00E+02 | 1.54 | 97.12% | 2.99 | 99.90% |
| Silver | 2 Hour | <10 | 3.92 | 99.99% | 4.29 | 99.99% |
| Treated | 4 Hour | <10 | 2.58 | 99.74% | 4.29 | 99.99% |
| | 6 Hour | <10 | 2.84 | 99.86% | 4.29 | 99.99% |

Study ID NG3265

| Sample | Time Point | CFU/Sample | R Value (Log10 Reduction) | Percent Reduction |
|---|---|---|---|---|
| Control | Time Zero | 2.08E+05 | N/A | |
| | 24 Hour | 3.25E+06 | | |
| Silver Treated | 24 Hour | <10 | 5.51 | >99.999% |

Bacterial inoculum preparations and subsequent recovery after UV exposure through the prototype ultraviolet test unit were performed by technicians of Environmental Safety Technologies, Inc. (EST). Direct operation of the UV test unit was performed alongside laboratory personnel by Guillermo Cohen of Alcavis.

Two glass microscope slides were placed side by side lengthwise and taped together using transparent tape. In the center of each slide, a one inch by one inch test area for inoculation with bacteria was drawn. A strip of vinyl, white tape was applied to one side. The connected slides were flipped over and one end of each side was marked as either top or bottom.

The experimental challenge organism of this experiment was the bacterium Methicillin-resistant *Staphylococcus aureus*, aka MRSA (ATCC 700698), Vancomycin Resistant *Enterococcus faecium*, aka VRE (ATCC 700221), *Acinetobacter baumanii* (ATCC 19609). Bacteria were grown overnight in Trypticase Soy Broth at 33 degrees Celsius.

The experimental challenge organism of this experiment was the bacterium *Clostridium difficile* (ATCC 700057). Bacteria were grown on BHIS agar medium containing 0.1% taurocholate plates for a sufficient time to induce uniform sporulation. The bacteria were then washed off the agar plate into sterile distilled water and stored at 4 degrees Celsius until use. A Gram-stain examination of the suspension confirmed that >95% of the bacterial cells contained a spore.

One hundred microliters of this bacterial stock suspension prepared with the addition of 5% heat inactivated serum (MP Biomedicals Product No. 2921149) was applied to each 1 inch×1 inch area test surface of both the top and bottom marked slides (pre-cleaned with alcohol). The inoculum was then streaked over each surface with a sterile applicator and allowed to air dry (~45 minutes) at room temperature.

Inoculated surfaces were folded backwards, providing both a top and bottom test surface when placed on the UV unit's rollers. Each prepared slide was handed off and run through the ultraviolet lamp prototype unit. After a 20 second total cycle time, the slide was immediately returned to a laboratory technician for bacteria recovery.

A sterile, Dacron™ swab, wetted after dipping into a tube containing 1 ml of sterile water, was used to recover bacteria from inoculated top and bottom slide surfaces. Swabs were vortexed in the same tube of remaining 1 ml sterile water, plated on trypticase soy agar, incubated overnight at 33 degrees Celsius, and counted to obtain the number of surviving viable bacteria.

TABLE

Glass Slides Results in Preproduction System

| Material | Glass Slides | | |
|---|---|---|---|
| Organism | Initial Count | Final Count | Reduction |
| *Geobacillus*\* | 300000 | 27 | 99.99100% |
| MRSA\* | 450000 | 0 | >99.99978% |
| VRE\* | 400000 | 5 | 99.99875% |
| *Acinetobacter*\* | 8500 | 0 | >99.98824% |
| C. Diff\*\* | 4000 | 0 | >99.97500% |

\*Average of both Initial counts, and Final counts respectively
\*\*Average of both Initial counts, and Final counts respectively in faster run experiment While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An appliance for disinfecting hand-held devices each having a surface that is contacted manually when the device is in use, comprising:
    a source of disinfecting radiation; and
    a conveyer system operative to convey the devices past the source with at least one surface of each device facing the source, wherein:
    said conveyor system comprises a plurality of hollow, transparent rollers, and
    said source of disinfecting radiation comprises a first plurality of lamps each housed in a respective ones of said transparent rollers.

2. The appliance of claim 1, wherein each of said lamps produces UV-C radiation.

3. The appliance of claim 2, wherein each of said lamps produces radiation at a wavelength of 100-290 mm.

4. The appliance of claim 3, wherein each of said lamps produces radiation having a wavelength of about 254 mm.

5. The appliance of claim 1, wherein each of said rollers is made of quartz.

6. The appliance of claim 1, further comprising a housing having an open top and a lid for closing said upper top, said lid being connected to said base by a hinge.

7. The appliance of claim 6, further comprising at least one safety device connected to turn off said lamps in response of opening of said lid.

8. The appliance of claim 1, wherein said conveyor system has an inlet end and an outlet end between which said lamps are disposed, said appliance has an inlet opening at said inlet end of said conveyor system and an outlet opening at an outlet end of said conveyor system, and said appliance further comprises a UV radiation blocking system enclosing said lamps to minimize the escape of radiation through said inlet and outlet openings.

9. The appliance of claim 8, wherein said conveyor system defines a conveying path between said inlet and outlet openings, and said UV radiation blocking system comprises a plurality of curtains extending across the conveying path.

10. The appliance of claim 1, further comprising a second plurality of lamps located above said first plurality of lamps, and wherein said conveyor system is operative to convey devices between said first plurality of lamps and said second plurality of lamps.

11. The appliance of claim 10, wherein each of said lamps of said second plurality produces UV-C radiation.

12. The appliance of claim 11, further comprising an inner lid member carrying said second plurality of lamps, said inner lid member being pivotally mounted to said base.

\* \* \* \* \*